United States Patent [19]

Fleming

[11] 4,380,548
[45] Apr. 19, 1983

[54] N-(2,6-DIMETHYLPHENYL)-4,5-DIHYDRO-4,4-DIALKYL-2-METHYLTHIO-1H-IMIDAZOLE-1-CARBOXAMIDES, ANTICONVULSIVE COMPOSITION AND METHOD

[75] Inventor: Robert W. Fleming, Ann Arbor, Mich.

[73] Assignee: Warner-Lambert Company, Morris Plains, N.J.

[21] Appl. No.: 296,764

[22] Filed: Aug. 27, 1981

[51] Int. Cl.³ .................... A61K 31/415; C07D 233/42
[52] U.S. Cl. ................................ 424/273 R; 548/351; 548/320
[58] Field of Search ...................... 548/351; 424/273 R

[56] References Cited
U.S. PATENT DOCUMENTS 3,174,975  3/1965  Langis et al. ......................... 548/351
3,536,714  10/1970  Eberle ................................. 548/351
4,226,876  10/1980  Copp et al. .......................... 548/351

OTHER PUBLICATIONS

Wisterowicz et al., Chem. Abst. 1981, vol. 94, No. 30648a.
Wisterowicz et al., Acta Polon. Pharm. 1979, vol. 36 (1), pp. 25-32.

Primary Examiner—Henry R. Jiles
Assistant Examiner—Natalia Harkaway
Attorney, Agent, or Firm—Ronald A. Daignault

[57]  ABSTRACT

The invention provides new N-(2,6-dimethylphenyl)-2-methylthio-1-imidazolidinecarboxamides and their pharmaceutically acceptable salts which are useful as anticonvulsant agents. Also provided are methods for preparing the compounds of the invention, pharmaceutical compositions containing said compounds and methods for using said compositions.

5 Claims, No Drawings

N-(2,6-DIMETHYLPHENYL)-4,5-DIHYDRO-4,4-DIALKYL-2-METHYLTHIO-1H-IMIDAZOLE-1-CARBOXAMIDES, ANTICONVULSIVE COMPOSITION AND METHOD

BACKGROUND OF THE INVENTION

The compounds of the invention are new and are useful as anticonvulsant agents. The most closely structurally related prior art compounds of which the applicant is aware are disclosed in Acta Pol. Pharm., 36, 25(1979).

SUMMARY OF THE INVENTION

The invention sought to be patented in its generic compound aspect is a compound having the structural formula I:

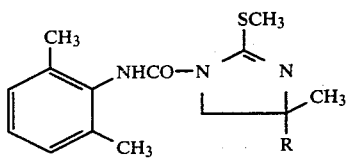

wherein R is hydrogen or methyl, and the pharmaceutically acceptable salts thereof.

The invention sought to be patented in its first specific compound aspect is a compound having the structural formula:

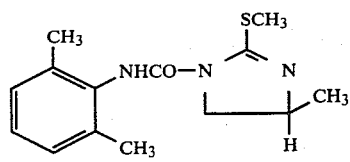

and the pharmaceutically acceptable salts thereof.

The invention sought to be patented in its second specific compound aspect is a compound having the structural formula:

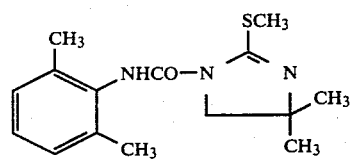

and the pharmaceutically acceptable salts thereof.

The invention sought to be patented in its first chemical process aspect is a process for preparing a compound having the structural formula:

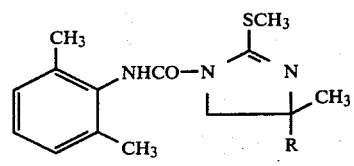

wherein R is hydrogen or methyl which comprises reacting a compound having the structural formula:

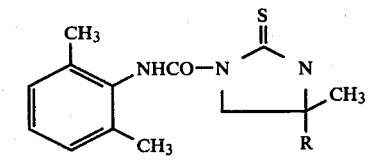

wherein R is hydrogen or methyl with a methylating agent; and isolating the product.

The invention sought to be patented in its second chemical process apsect is a process for preparing a compound having the structural formula:

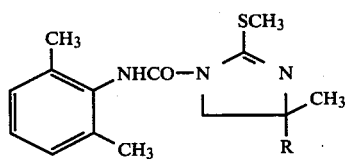

wherein R is hydrogen or methyl which comprises reacting a compound having the structural formula:

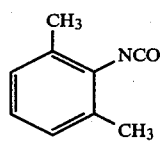

with a compound having the structural formula:

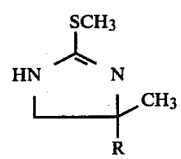

wherein R is hydrogen or methyl; and isolating the product.

The invention sought to be patented in a pharmaceutical composition aspect is a composition useful for treating or preventing convulsion in a mammal, which composition consists essentially of a compound having the structural formula 1 or mixtures thereof, in combination with the pharmaceutically acceptable carrier.

The invention sought to be patented in a pharmaceutical method aspect is a method for treating or preventing convulsions in a mammal in need of such treatment; which comprises administering an anticonvulsive effective amount of the above defined pharamaceutical composition to said mammal.

DESCRIPTION OF THE PREFERRED EMBODIMENTS

The compounds of the invention may be prepared by any of several processes which are to be considered as equivalent for purposes of this invention.

One such process involves the reaction between an imidazolidine-2-thione having the structural formula

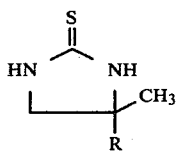

with 2,6-dimethylphenyl isocyanate. This reaction is conveniently carried out at elevated temperature in a non-reactive solvent such as dimethylformamide. The product of this reaction, an N-(2,6-dimethylphenyl)-2-thioxo-1-imidazolidinecarboxamide, is next methylated with a methylating agent, such as methyliodide or dimethylsulfate using well known procedures.

In an alternate process, the imidazolidine-2-thione may first be methylated with a methylating agent such as methyliodide prior to its reaction with 2,6-dimethylphenyl isocyanate.

The starting compound 2,6-dimethylphenyl isocyanate is commercially available and may also be conveniently prepared by the method described in Organic Synthesis, Collective Vol. II, p. 453, John Wiley and Sons, Inc., New York, 1943. The substituted imidazolidine-2-thiones may be conveniently prepared by the method described in Organic Synthesis, Collective Vol. III, p. 394, John Wiley and Sons, Inc., New York, 1955.

The compounds of the invention form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, malonic, ascorbic, maleic methanesulfonic and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

Selected compounds of the invention may exist in optical isomeric forms. For purposes of the invention, the individual pure isomers as well as mixtures thereof are considered to be equivalent.

The compounds of the invention are new chemical substances of value as pharmacological agents for the treatment or prevention of convulsions in warm-blooded animals. The anticonvulsant activity of the compounds of the invention was established by the following test procedure:

The test compound is dosed intraperitoneally as a solution in water or as a suspension in 0.2% methocel to a group of 10 mice, 30 minutes before shocking. The mice are Swiss Webster, male, 25–30 grams. The shock is administered via ear clips at 25 mA for 250 m sec. 60Hz. Unprotected animals respond to the shock with a tonic extensor seizure. Compounds which display activity at levels below 100 mg/kg are considered active. Using the above test procedure, the following results were obtained for the compounds of the invention.

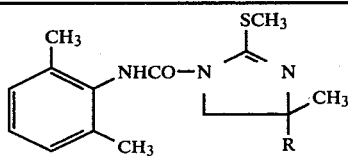

| R | DOSE mg/kg | No. Protected/ No. Tested |
| --- | --- | --- |
| CH$_3$ | 60 | 10/10 |
| as | 40 | 10/10 |
| Free Base | 20 | 7/10 |
|  | 15 | 3/10 |
|  | 10 | 1/10 |
| H | 30 | 5/5 |
| as | 10 | 0/5 |
| Free Base |  |  |
| CH$_3$ | 14 | 10/10 |
| as | 10 | 8/10 |
| HCl | 8 | 8/10 |
| Salt | 6 | 3/10 |
|  | 4 | 0/10 |

The compounds of the invention can be prepared and administered in a wide variety of oral and parenteral dosage forms. It will be clear to those skilled in the art that the following dosage forms may comprise as the active component, either a compound of formula I, or a corresponding pharmaceutically acceptable salt of a compound of formula I, or a mixture or such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeniously therein as by stirring. The molten homogenious mixture is then poured into convenient sized molds, allowed to cool and thereby to solidify.

Liquid form preparations include solutions, suspensions and emulsions. As an example may be mentioned water or waterpropylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeterers, dispersants, thickeners, solublizing agents and the like. The liquid utilized for preparing the liquid form preparation may be water, isotonic water, ethanol, glycerine, propylene glycol and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

In therapeutic use as agents for treating convulsions in mammals, the compounds utilized in the pharmaceutical method of this invention are administered at the initial dosage of about 1.0 mg to about 1000 mg per kilogram daily. A daily dose range of about 15 mg to about 400 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following non-limiting examples illustrate the inventor's preferred methods for preparing the compounds of the invention.

EXAMPLE 1

Preparation of N-(2,6-dimethylphenyl)-4,5-dihydro-4,4-dimethyl-2-(methylthio)-1H-imidazole-1-carboxamide, hydroiodide, free base, and hydrochloride A mixture of 37.8 g (0.14 M) of the thione from Preparative Example 1, 500 ml methanol and 27.8 g (0.19 M) methyliodide was refluxed with stirring for 16 hours. The resulting slightly turbid solution was cooled to room temperature and filtered through a celite pad to clarify. After concentration to approximately 150 ml volume and cooling to 5° C., a crop of crystals was filtered off, washed with cold methanol, and dried in vacuo at 45° C. Yield of N-(2,6-dimethylphenyl)-4,5-dihydro-4,4-dimethyl-2-(methylthio)-1H-imidazole-1-carboxamide, hydroiodide was 33 g, mp 156°–157.7° C. An analytical sample was obtained by recrystallizing from methanol, mp 157°–158° C.

The above hydroiodide was converted to free base by mixing with a small excess of cold sodium hydroxide solution and extracting with chloroform. The chloroform extracts were washed with water, dried over anhydrous magnesium sulfate, filtered, and the solvent removed on a rotary evaporator. The solid residue was recrystallized from approximately 1 liter of ethyl acetate to yield N-(2,6-dimethylphenyl)-4,5-dihydro-4,4-dimethyl-2-(methylthio)-1H-imidazole-1-carboxamide, free base as glistening white plates, mp 178°–179° C. An analytical sample obtained by a second recrystallization melted at 179°–180° C.

Conversion of the above free base to hydrochloride was accomplished by suspending in 100 ml chloroform, acidifying with a slight excess of 6 N hydrogen chloride in isopropanol, and dilution with two volumes of anhydrous ether. After cooling, the product was filtered, washed with anhydrous ether, and dried in vacuo at 45° C. Yield of N-(2,6-dimethylphenyl)-4,5-dihydro-4,4-dimethyl-2-(methylthio)-1H-imidazole-1-carboxamide, hydrochloride was 24.5 g, mp 131°–135° C. Recrystallization from 75 ml absolute alcohol plus 50 ml anhydrous ether gave pure product melting at 138°–139° C. The compound is a white crystalline solid which yields a clear and colorless 10% solution in water.

EXAMPLE 2

Preparation of N-(2,6-dimethylphenyl)-4,5-dihydro-4,4-dimethyl-2-methylthio-1H-imidazole-1-carboxamide HCl A suspension of 68.0 g (0.25 M) of 4,4-dimethyl-2-(methylthio)imidazoline hydroiodide from Preparative Example 2 in 1 liter of dry tetrahydrofuran is treated with 34.9 ml (0.25 M) triethylamine, then a solution of 36.8 g (0.25 M) 2,6-dimethylphenyl isocyanate in an equal volume of THF is dropped in with good stirring over 15 minutes. The mixture is stirred at room temperature for 2 hours, filtered, and the filter cake of Et$_3$N.HI washed with THF. The filtrate is evaporated to remove all solvent and the solid residue dissolved in about 500 ml methylene chloride. This solution is washed two times with water and dried over anhydrous MgSO₄. After filtering and stripping the CH₂Cl₂, the solid residue is dissolved in about 1.5 liters of boiling ethyl acetate. Upon cooling in an ice bath, the product N-(2,6-dimethylphenyl)-4,5-dihydro-4,4-dimethyl-2-methylthio-1H-imidazole-b 1-carboxamide crystallizes and is filtered and dried at 45° C. in vacuo. Yield 53.7 g, mp 178°–179° C. A second crop of 11.7 g, mp 178°–179° C., is obtained by concentrating the filtrate to 200 ml. Total yield 64.8 g.

The base as obtained above is converted to hydrochloride by suspending 100 g in 1 liter methylene chloride. Acidify with the stochiometric quantity of HCl in isopropanol (65 ml of ca 5 N soln.). The resulting pH is about 2.5 and the solution is clear. Dilute while still warm to 2 liters with anhydrous ether, seed, and cool in ice. Filter and wash with dry ether. The Yield of N-(2,6-dimethylphenyl)-4,5-dihydro-4,4-dimethyl-2-methylthio-1H-imidazole-1-carboxamide HCl is 115.4 g, mp 119°–129° C. This salt is recrystallized by dissolving in three volumes of absolute 3A alcohol at temperatures below 50° C. and diluting while warm with two volumes of dry ether. On cooling in ice, a good recovery of nicely crystalline product is obtained. The pure material has a melting point of 138°–139° C.

EXAMPLE 3

Preparation of N-(2,6-dimethylphenyl)-4,5-dihydro-4-methyl-2(methylthio)-1H-imidazole-1-carboxamide The subject compound is obtained by the same procedure as given in Example 2 starting with 4-methyl-2-(methylthio)imidazoline hydroiodide prepared in Preparative Example 3. The free base N-(2,6-dimethylphenyl)-4,5-dihydro-4-methyl-2(methylthio)-1H-imidazole-1-carboxamide melts at 144°–144.5° C.

PREPARATIVE EXAMPLE 1

Preparation of N-(2,6-dimethylphenyl)-4,4-dimethyl-2-thioxo-1-imidazolidinecarboxamide A mixture of 39.0 g (0.3 M) 4,4-dimethylimidazolidine-2-thione, 44.2 g (0.3 M) 2,6-dimethylphenyl isocyanate and 100 ml dimethylformamide was refluxed with stirring for 24 hours. After cooling to room temperature, the solution was filtered from a small amount of insoluble solid and poured into 300 ml water with efficient stirring. The precipitated product was filtered, washed well with water, and dried in vacuo. Yield 62.6 g, mp 228°–231° C. Recrystallization from 600 ml of boiling methanol yielded 46 g of N-(2,6-dimethylphenyl)-4,4-dimethyl-2-thioxo-1-imidazolidinecarboxamide as white crystalline product, mp 241.5°–243° C. A small sample was recrystallized from benzene to give an analytical sample, mp 245.5°–246° C.

PREPARATIVE EXAMPLE 2

Preparation of 4,4-dimethyl-2-(methylthio)imidazoline hydroiodide

A suspension of 110 g (0.83 M) of 4,4-dimethyl-2-imidazolidinethione in 700 ml isopropanol was treated with 148 g (1.04 M) methyl iodide and stirred at room temperature under reflux for ½ hour. When all had dissolved, heated to gentle reflux for 1 hour. Cool, dilute to 2 liters with anhydrous ether, seed, and cool in ice. Filter and wash with dry ether. Yield of 4,4-dimethyl-2-(methylthio)imidazoline hydroiodide was 221 g, 98%, mp 93.5°–95° C. Pure material melts at 94.5°–95° C.

PREPARATIVE EXAMPLE 3

Preparation of 4-methyl-2-(methylthio)-imidazoline hydroiodide

This material is prepared by the same procedure as given in Preparative Example 2 starting with 4-methyl-2-imidazolidinethione. The product 4-methyl-2-(methylthio)-imidazoline hydroiodide melts at 91°–92° C.

I claim:

1. A compound having the structural formula

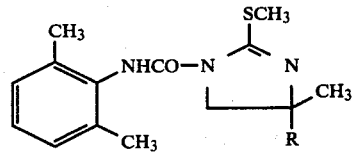

wherein R is hydrogen or methyl, and the pharmaceutically acceptable acid addition salts thereof.

2. The compound defined in claim 1 which is N-(2,6-dimethylphenyl)-4,5-dihydro-4,4-dimethyl-2-(methylthio)-1H-imidazole-1-carboxamide, and the pharmaceutically acceptable acid addition salts thereof.

3. The compound defined in claim 1 which is N-(2,6-dimethylphenyl)-4,5-dihydro-4-methyl-2-(methylthio)-1H-imidazole-1-carboxamide, and the pharmaceutically acceptable acid addition salts thereof.

4. A pharmaceutical composition useful for treating or preventing convulsions in a mammal which composition consists essentially of an anticonvulsive effective amount of a compound defined in claim 1 or mixtures thereof, in combination with a pharmaceutically acceptable carrier.

5. A method for treating or preventing convulsions in a mammal in need of such treatment which comprises administering an anticonvulsive effective amount of the pharmaceutical composition defined in claim 4 to said mammal.

* * * * *